(12) United States Patent
DiTizio et al.

(10) Patent No.: US 8,840,927 B2
(45) Date of Patent: *Sep. 23, 2014

(54) METHOD OF MAKING ANTI-MICROBIAL POLYMERIC SURFACES

(75) Inventors: Valerio DiTizio, Toronto (CA); Frank DiCosmo, Richmond Hill (CA)

(73) Assignee: Covalon Technologies Inc., Mississauga, ON (CA)

( * ) Notice: Subject to any disclaimer, the term of this patent is extended or adjusted under 35 U.S.C. 154(b) by 1739 days.

This patent is subject to a terminal disclaimer.

(21) Appl. No.: 10/468,438

(22) PCT Filed: Feb. 26, 2002

(86) PCT No.: PCT/CA02/00246

§ 371 (c)(1),
(2), (4) Date: Jan. 5, 2004

(87) PCT Pub. No.: WO02/070022

PCT Pub. Date: Sep. 12, 2002

(65) Prior Publication Data

US 2004/0086568 A1    May 6, 2004

Related U.S. Application Data

(60) Provisional application No. 60/271,702, filed on Feb. 28, 2001.

(51) Int. Cl.
| | | |
|---|---|---|
| *A61L 27/00* | (2006.01) | |
| *A61L 29/16* | (2006.01) | |
| *A61L 27/54* | (2006.01) | |
| *A61L 27/34* | (2006.01) | |
| *A61L 31/16* | (2006.01) | |
| *A61L 29/08* | (2006.01) | |
| *A61L 31/10* | (2006.01) | |

(52) U.S. Cl.
CPC .................. *A61L 31/10* (2013.01); *A61L 29/16* (2013.01); *A61L 27/54* (2013.01); *A61L 27/34* (2013.01); *A61L 2300/606* (2013.01); *A61L 31/16* (2013.01); *A61L 29/085* (2013.01); *A61L 2300/104* (2013.01); *A61L 2300/404* (2013.01)
USPC .......................................... 424/486; 424/618

(58) Field of Classification Search
CPC ....................................................... A61L 27/34
USPC .................................................. 424/486, 618
See application file for complete search history.

(56) References Cited

U.S. PATENT DOCUMENTS

| | | | | |
|---|---|---|---|---|
| 4,603,152 A | * | 7/1986 | Laurin et al. | ................... 604/265 |
| 5,788,687 A | * | 8/1998 | Batich et al. | ............... 604/890.1 |
| 5,885,566 A | | 3/1999 | Goldberg | |
| 6,248,811 B1 | | 6/2001 | Ottersbach et al. | |
| 6,716,895 B1 | * | 4/2004 | Terry | ............................ 523/122 |

FOREIGN PATENT DOCUMENTS

| | | | |
|---|---|---|---|
| EP | 0 872 512 A | 10/1998 | |
| JP | A S55-078027 | 6/1980 | |
| JP | 5184665 | 7/1993 | |
| JP | 5309131 | 11/1993 | |
| JP | A H08-049247 | 2/1994 | |
| JP | A H07-016291 | 1/1995 | |
| JP | A H11-080394 | 3/1999 | |
| WO | WO 98/46287 | * 10/1998 | .............. A61L 27/00 |
| WO | WO 98 46287 A | 10/1998 | |
| WO | WO 9846287 A2 | * 10/1998 | |
| WO | WO 00 09173 A | 2/2000 | |

OTHER PUBLICATIONS

Ditizio V et al: "A liposomal hydrogel for the prevention of bacterial adhesion to catheters", (1998).

* cited by examiner

*Primary Examiner* — Jake Vu
(74) *Attorney, Agent, or Firm* — Sim & McBurney

(57) ABSTRACT

The present invention is a method for the modification of the surfaces of polymeric materials with polymer coatings that may be subsequently treated to be lubricious and anti-microbial. The method comprises incubating a photo-initiator-coated polymeric material with an aqueous monomer that is capable of free radical polymerization and exposing the incubating polymeric material to UV light creating a modified surface on said polymeric material. The method may additionally comprise adding a silver component to the modified surface. The silver component may be provided as a silver salt coating or a silver salt contained within a hydrogel bonded to the acrylate modified polymeric material surface.

15 Claims, 8 Drawing Sheets

METHOD OF MAKING ANTI-MICROBIAL POLYMERIC SURFACES

FIELD OF THE INVENTION

The present invention relates to methods for making modified polymeric surfaces and in particular, modified lubricious anti-microbial polymeric surfaces. Specifically, the present invention is directed to methods for the modification of the surfaces of polymeric materials with acrylic polymer coatings that may be subsequently treated to produce a low friction anti-microbial surface.

BACKGROUND OF THE INVENTION

Throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure.

The use of implanted medical devices is a vital component of current clinical practice, however, complications may arise from their use. Common complications are the physical trauma to the patient's tissues resulting from insertion and continued use of the device, as well as the potential for the device to serve as a focus for microbial contamination and thus, a possible source for microbial infection of the patient. In fact, these complications are often associated since the placement of a medical device, such a urethral catheter or ureteral stent, may cause tearing and bleeding of delicate tissues thereby creating an opportunity for infection through microbial contamination of the device or through subsequent migration of microbes along the device's surface. It has therefore been an object to develop better quality indwelling biomedical devices made from materials that provide for clinical advantages to a patient.

In response to the problem of insertion-related trauma, polymeric medical devices have been coated with various hydrophilic polymers to produce a more low friction or lubricious coating on the device. The coated devices have high friction surfaces when dry, but upon wetting the device becomes slippery and can be more readily inserted into veins, arteries, and other passageways causing minimal tissue damage. However, the methods to apply hydrophilic-coating processes as well as the coatings themselves possess several distinct disadvantages, any one of which can significantly diminish the value of the end product. First, and perhaps foremost, is the inability to produce a permanent lubricious coating, as many coatings will erode after only a limited exposure to an aqueous environment (1). Also, most of the current coating processes are resource-intensive procedures since they consist of at least two steps that require multiple compounds and organic solvents to produce the lubricious layer (2-4). Finally, many processes are incompatible with the use of various bio-active agents since they involve the use of organic solvents or a high temperature curing step (5,6). Even if the bio-active agent is compatible with other components of the coating, the capacity of the lubricious coating to allow for extended release of the agent is often limited because either the coating sloughs off or there is little inherent affinity between the coating and the agent.

Many of the polymers used to make medical devices are chemically inert requiring the introduction of reactive chemical groups to the polymeric surface in order to provide a more desirable bioactive surface. There are reports describing surface modification of polymers containing reactive functional groups introduced through the inclusion of derivatized monomers in the initial polymer formulation (7-9). While this approach may yield adequate results, there are issues of convenience and the bulk properties of the polymer may be adversely affected. Similarly, surface modification using plasma discharge (10) and γ-irradiation (11) techniques as described for example in U.S. Pat. No. 5,885,566 may not always be practical because of the need for specialized equipment and the propensity for alteration of bulk material properties. Also, none of the above-mentioned procedures allow for precise spatial control of the surface modification reaction.

Surface graft polymerization using long-wave ultraviolet (UV) light has been shown to be an efficient and convenient method for modifying polymer surfaces with the added benefit of micro-regional control through the use of projection masks (12). One common strategy for surface photografting uses benzophenone and related molecules to abstract hydrogen atoms from the polymer surface, thereby creating surface-bound radicals capable of initiating graft polymerization of monomers in the vapour phase or in solution (13,14). U.S. Pat. No. 6,248,811 discloses surface grafting of a coating polymer to a portion of the a surface of a substrate using UV radiation. The resultant surface may be antibacterial and further inhibit or promote cell proliferation.

Attempts have also been made to add anti-microbial agent(s) to a surface modified polymer as is disclosed for example in U.S. Pat. No. 5,788,687 in which the anti-microbial agents acetohydroxamic acid and magnesium ammonium phosphate hexahydrate are released upon a change of pH from a polymer hydrogel that is coated onto a polymeric surface.

Silver is known to have general anti-microbial properties directed against a wide range of bacteria and fungi and has been used for many years in clinical settings and particularly on a wide range of medical devices which include coatings for catheters, cuffs, orthopedic implants, sutures, dental amalgams and wound dressings. As a coating on catheters silver has been demonstrated to reduce the incidence of infection associated with the use of such devices. Both silver alloy and silver oxide has been used to coat urinary catheters and are somewhat effective in preventing urinary tract infections (15). However, the use of silver as a prophylactic against infection in general, has not found widespread application because of problems associated with inadequately coating device surfaces, poor solubility of metallic silver and silver oxides, short half-life, rapid binding of silver ions and inactivation by proteins and light-mediated inactivation and discoloration, and slow release of silver ions from the metallic complex.

Thus, there is a need to develop a method to effectively modify the surface of polymeric materials, which form the basis for clinically used medical devices, in a manner such that the surface is lubricious and can further be modified to have anti-microbial properties in a manner that obviates at least one problem with that of the prior art.

SUMMARY OF THE INVENTION

The present invention provides methods for making modified polymeric surfaces and furthermore, modified lubricious and anti-microbial polymeric surfaces on polymeric materials. Specifically, the present invention provides methods for the modification of the surfaces of polymeric materials with stable polymer coatings to make the surfaces more biocompatible and lubricious and further can be subsequently treated with a desired silver agent or silver component in order to produce a lubricious anti-microbial surface.

The methods of the invention preferably aim to modify the surfaces of a wide variety of polymeric materials such as for example silicone rubber that are used clinically in vivo with polymer coatings treated with silver salts for the provision of anti-microbial surfaces in order to prevent, ameliorate and treat bacterial and fungal infections in humans and mammals. One skilled in the art would readily comprehend the scope of polymeric materials that can be modified in accordance with the present invention.

According to one embodiment of the present invention, a hydrophilic poly-acrylate-modified polymeric surface is provided. In a further embodiment of the present invention the acrylate coating of the polymeric surface is used to retain a silver component that is released in order to treat and help prevent bacterial and fungal infections. In still another embodiment of the present invention the acrylate-modified silicone surface has incorporated therein a silver component within a polyethylene oxide hydrogel capable of releasing silver. In one aspect of this embodiment, the silver component is provided encapsulated with liposomes that are provided within the polyethylene oxide hydrogel.

The silver component for use in the invention can comprise a variety of different formats. Preferably, the silver component is a silver salt. Most preferred silver salts for use in the present invention include silver phosphate, silver citrate and silver lactate, however, other silver salts are suitable for use in the present invention and include but are not limited to silver acetate, silver benzoate, silver chloride, silver carbonate, silver iodide, silver iodate, silver nitrate, silver laurate, silver sulfadiazine, silver palmitate and mixtures thereof.

In accordance with an aspect of the present invention is a method for making a modified surface on a polymeric material, the method comprising:

incubating a photo-initiator-coated polymeric material with an aqueous monomer capable of free radical polymerization; and exposing the incubating polymeric material to UV light creating a modified surface on said polymeric material.

According to yet a further aspect of the present invention is a polymeric composite comprising;

a polymeric body having a stable polyacrylate modified surface, said surface being hydrophilic, lubricious and anti-microbial.

According to a further aspect of the present invention is a polyacrylate coated polymer.

According to a further aspect of the present invention is an anti-microbial polyacrylate coated polymer having a silver component within the polyacrylate coating.

According to a further aspect of the present invention is an anti-microbial polyacrylate coated polymer having a silver component within the polyacrylate coating, wherein the silver component is released from the polyacrylate coating continuously over a period of time.

According to another aspect of the invention is a method for making a lubricious modified surface on a polymeric material, the method comprising;

incubating a photo-initiator-coated polymeric material with an aqueous monomer capable of free radical polymerization;

exposing the incubating polymeric material to UV light creating a modified surface on said polymeric material;

rendering said modified surface lubricious.

According to a further aspect of the present invention is a method for making a lubricious anti-microbial modified surface on a polymeric material, the method comprising:

incubating a photo-initiator-coated polymeric material with an aqueous monomer capable of free radical polymerization;

exposing the incubating polymeric material to UV light creating a modified polymeric surface on said polymeric material;

rendering said modified surface lubricious; and adding a silver agent to said lubricious modified polymeric surface.

According to another aspect of the present invention is a method for making a lubricious anti-microbial modified surface on a polymeric material, the method comprising:

precoating a polymeric material with a photo-initiator;

immersing the precoated polymeric material in an aqueous solution of vinyl carboxylic acid monomer and exposing the incubating polymeric material to UV light to create a modified non-lubricious polyacrylate surface on said polymeric material;

ionizing said polyacrylate surface of said polymeric material by immersion in an aqueous base;

saturating the polyacrylate surface with cations by immersion in an electrolyte solution; and providing silver to said cation-saturated polyacrylate surface.

The silver may be provided as a coating or incorporated within a hydrogel bonded to the acrylate modified polymeric material surface.

The methods of the present invention has particular use for providing anti-microbial polymeric materials, preferably silicone materials and most preferably poly(dimethylsiloxane)-based polymers. Such polymers are typically used clinically in a variety of medical devices including in-dwelling medical devices and devices in general which include but are not limited to dressings, pins, clips, cathers, stents, implants, tubings and the like. The method can be conveniently used with a wide variety of silver salts leading to the slow and continued release of the silver from the surface of the device for a long effective period of time. The method conveniently loads a great amount of silver such that it can be released for a long and effective period of time.

BRIEF DESCRIPTION OF THE DRAWINGS

The present invention will be further understood from the following description with reference to the Figures, in which.

Figure 1:
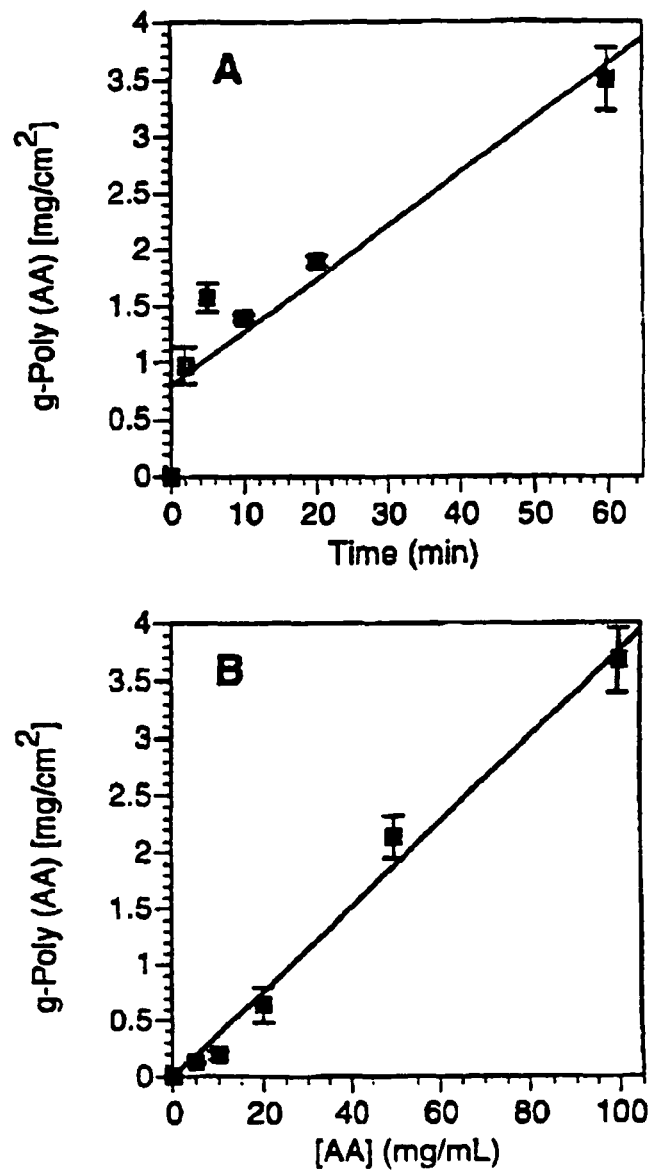
FIG. 1(A) shows the amount of poly (acrylic acid [AA]) grafted onto poly (dimethylsiloxane) [PDMS] as a function of UVA irradiation time. Samples were initially coated with 10 mM p-benzoyl tert-butylperbenzoate (BPB). AA concentration in the BPB-saturated aqueous solution was 50 mg/mL (694 mM).
FIG. 1(B) shows poly (AA) grafting extent with respect to initial monomer concentration. Samples were coated with 10 mM BPB and exposed to UVA light for 20 minutes.
Figure 2:
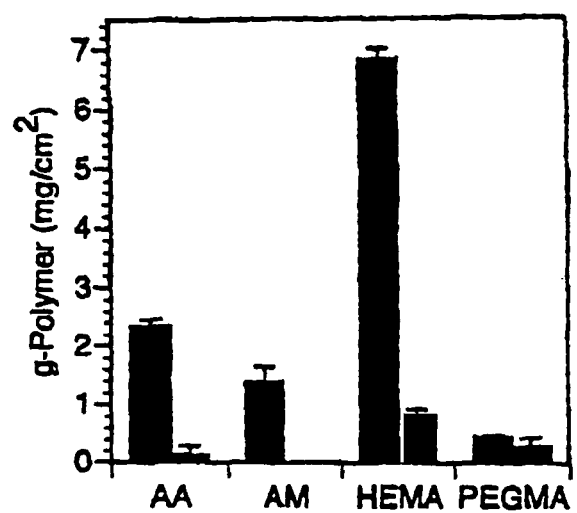
FIG. 2 shows grafting yields of various polymers onto PDMS as a function of BPB pre-coating (100 mM) or BPB presence in the monomer solution. Monomer concentration was 694 mM and samples were exposed to UVA light for 20 minutes.

In the drawings, preferred embodiments of the invention are illustrated by way of example. It is to be expressly understood that the description and drawings are for the purpose of illustration and as an aid to understanding, and are not intended as a definition of the limits of the invention.

DETAILED DESCRIPTION OF THE PREFERRED EMBODIMENTS

The present invention provides a mild, efficient and effective method for permanently modifying the surface of chemically inert polymers with polyacrylate coatings that can be made lubricious and endowed with anti-microbial properties. As such, the method provides for a polymeric composite that has a stable hydrophilic bio-active surface which can be further provided to possess the characteristics of lubricity and anti-microbial properties.

The chemically inert polymers for use in the invention are those that are used and desirable to fabricate various types of in-dwelling devices. Examples of in-dwelling devices include but are not limited to implants, catheters, stents, wound dressing, cardiac valves, pins, clamps, tubings and the like can be used in the practice of the invention. As such, polymers that can be surface modified according to the present invention include all polymeric substrates such as polyurethanes, polyamides, polyesters, polyethers, polyorganosiloxanes, polysulfones, polytetrafluoroethylene, polysiloxanes and the like.

The method specifically involves adding hydrophilic coatings such as polyacrylate to the surface of inert polymers such as poly (dimethylsiloxane)-based polymers (silicone) through the use of long wavelength UV radiation (300-400 nm) and a photo-initiator such as for example p-benzoyl tert-butylperbenzoate (BPB).

The method comprises an initial step of free radical-mediated graft polymerization of acrylic acid or various other acrylates on photo-initiator-coated polymer surfaces placed in aqueous solutions of monomer and exposed to UV light (365 nm). The photo-initiator is coated onto the surface of selected polymeric material by incubating the polymeric material in a methanolic solution of photo-initiator for a time sufficient that the photo-initiator will adhere to the polymeric surface. Any means of providing a photo-initiator coated polymeric material will work in the method of the present invention. This is followed by air-drying of the photo-initiator coated polymeric material.

When working with silicone as the substrate polymer, grafting levels of nearly 1 mg/cm2 are achieved with as little as 2 minutes of irradiation time using aqueous AA (5 wt %).

One skilled in the art can appreciate that the level of grafting may be controlled by adjustment of photo-initiator and monomer concentrations, as well as duration of irradiation. The poly (AA) coating so produced is hydrophilic but not very lubricious.

To produce a lubricous surface, the poly (AA) coating is ionized in an aqueous base solution having a pH of greater than about 8.0. Suitable aqueous bases for use include but are not limited to disodium tetraborate (borate buffer), sodium carbonate, hydroxides such ammonium hydroxide, calcium hydroxide, sodium hydroxide and mixtures thereof.

Ionization of the poly(AA) coating produces a negatively charged surface. The negatively charged surface is then saturated with cations to prepare the surface for coating with the antimicrobial agent. Saturation can be effected by immersion in an appropriate electrolyte solution such as for example but not limited to sodium lactate, sodium citrate, disodium phosphate, potassium lactate, potassium citrate, dipotassium phosphate and mixtures thereof. One skilled in the art would readily understand the type of cation-saturating electrolyte solution that can be used in the method of the invention. It is important to note however, that the nature of the anion of the cation saturating solution should be such that it forms a complex with silver ions that is at least slightly soluble. This is why sodium lactate works well because silver lactate is a relatively soluble salt.

Suitable photo-initiators for use in the methods of the invention include but are not limited to peresters, α-hydroxyketones, benzil ketals, benzoins and their derivatives and mixtures thereof. Specifically, suitable photo-initiators may be selected from 2,2-dimethoxy-2-phenyl-acetophenone (DPA), p-benzoyl tert-butylperbenzoate (BPB) and mixtures thereof. One skilled in art would readily understand the type of photo-initiator that can be used in the method of the invention.

Suitable monomers for use in the present invention for the modification of the polymeric material surfaces include but are not limited to monomers sensitive to the presence of free radicals, that is, monomers capable of free radical polymerization such as acrylic acid, methacrylic acid, 2-carboxyethyl acrylate, 4-vinylbenzoic acid, itaconic acid, and mixtures thereof. The preferred monomer is acrylic acid.

The UV radiation for use in the method of the invention can be for example in the wavelength range of about 100 nm to 400 nm, more preferably about 200 nm to 400 nm, and more preferably from 300 to 400 nm.

It is demonstrated that the photosensitive perester BPB leads to significant graft polymerization onto PDMS in a surface photografting reaction. It is further demonstrated that a BPB coating on PDMS can induce extensive graft polymerization of a number of hydrophilic monomers in an aqueous solution when exposed to 365 nm UV light.

In a further embodiment of the invention the surface modified material is incubated in a selected silver component such as a silver salt solution to produce an anti-microbial surface that releases silver ions. In one aspect, the ionized poly (AA) modified polymeric material is incubated in a concentrated solution of sodium lactate (0.1M to 1.0M) for about 10 to 60 minutes, most preferably about 30 minutes. The materials are then transferred to a selected silver salt solution (i.e. silver lactate) for about 5 to 120 seconds, preferably about 60 seconds, in order to produce an anti-microbial surface that retains silver ions and slowly releases them over an extended period. Should a silver solution be applied directly to the ionized polyacrylate coating then surface lubricity is lost. Therefore, pre-soaking in sodium lactate or any suitable cation-saturating electrolyte solution such as sodium acetate, sodium citrate, sodium benzoate, sodium salicylate, sodium thiosulfate, disodium phosphate and/or their potassium salt versions as is understood by one of skill in the art prior to application of a silver solution is required to maintain surface lubricity.

Without being constrained to any particular theory, the loss of lubricity may be explained by complex formation of the ionized polyacrylate carboxyl groups with positively charged silver ions; assuming that the surface lubricity is the result of the mutual repulsion of the many ionized polyacrylate chains grafted onto the substrate surface. Thus, the sodium lactate immersion step results in a large excess of sodium ions present in the polyacrylate coating which compete for carboxyl binding sites and prevent all of the silver ions binding to and deactivating the polyacrylate coating. The inability of sodium ions to reduce lubricity of polyacrylate coatings may be due to the much stronger affinity of polyacrylate carboxylates for silver ion. Also, silver ions may ligand multiple carboxylate sites.

In a further embodiment, the invention provides an acrylate-modified silicone surface to which a silver salt-containing liposome-gelatin-polyethylene oxide hydrogel is covalently attached to release silver ions for treating, ameliorating and/or preventing bacterial and fungal infections in humans and mammals. Polyacrylate-coated materials are activated for covalent binding to gelatin-poly (ethylene oxide) hydrogels by initial immersion in a solution of carbodiimide. The adhesion of the hydrogel coating to a surface-modified silicone material was found to increase approximately fifty-fold relative to unmodified silicone.

The binding of silver salts and the covalent binding of gelatin-poly (ethylene oxide) hydrogel containing silver salts encapsulated within liposomes to the surface of poly (acrylic acid)-grafted silicone samples acts to provide a source of readily available silver ions for the treatment and prevention of bacterial and fungal infections in humans and mammals. The manufacture and use of silver salts encapsulated within liposomes is disclosed in the co-inventor's co-pending U.S. Patent Application Serial No. 60/159,427 filed Oct. 14, 1999 (the entirety of which is herein incorporated by reference). The manufacture of liposome-poly (ethylene oxide)-gelatin hydrogel for use in the methods of the present invention is disclosed in co-owned U.S. Pat. No. 6,132,765 (the entirety of which is herein incorporated by reference). The adhesion of the hydrogel coating to the surface-modified silicone was found to increase approximately fifty-fold relative to unmodified silicone.

The silver component for use in the methods of the invention is a silver salt. Most preferred silver salts for use in the present invention include silver phosphate, silver citrate, silver lactate and mixtures thereof. However, other silver salts are suitable for use in the present invention and include but are not limited to silver acetate, silver benzoate, silver chloride, silver carbonate, silver iodide, silver iodate, silver nitrate, silver laurate, silver sulfadiazine, silver palmitate and mixtures thereof. The silver may be also incorporated within the hydrogel by encapsulation or association with pharmaceutical carriers such as liposomes, micelles, microcapsules, microspheres, nanospheres and mixtures thereof.

In summary, the methods of present invention provide a surface modified and lubricous polymeric material that has use as an in-dwelling device for a variety of different clinical applications. The methods are mild and efficiently modify polymeric surfaces in an easy and reliable manner. Furthermore, such surfaces are also provided as lubricious in order to facilitate their clinical in vivo use. Lastly, the modified surfaces may also be made to be antibacterial and/or anti-fungal in order to ameliorate and/or prevent and minimize and bacterial and/or fungal infection that can further compromise a patient.

EXAMPLES

The examples are described for the purposes of illustration and are not intended to limit the scope of the invention.

Methods of synthetic chemistry, biochemistry, molecular biology and histology referred to but not explicitly described in this disclosure and examples are reported in the scientific literature and are well known to those skilled in the art.

Example 1

Preparation of Acrylate-Modified Silicone Surface

Pre-weighed silicone disks (approximately 0.7 cm in diameter, 0.2 cm in thickness) or cylindrical sections (approximately 0.5 cm in diameter, 1 cm in length) were incubated in a methanol solution of photo-initiator (BPB; or p-benzoyl benzoic acid, BBA) for 1 hour followed by air drying at about 40° C. for 2 hours. Samples were then suspended in vials containing 3 mL of aqueous monomer solution. When required, monomer solutions were saturated with BPB. The aqueous solubility of BPB was 4 µg/mL. All solutions were filtered through 0.22 µm pore filters prior to being flushed with nitrogen for 15 min. Vials were sealed with rubber septa and placed 2.5 cm beneath a pair of UVA bulbs (15 W ea.). Radiation intensity at the sample site was 3.8 mW/cm2 as determined by UV actinometry (16). After completion of the graft polymerization reaction, samples were briefly washed under running water with occasional scrubbing to remove any signs of adsorbed homopolymer. The remaining non-grafted material was removed by overnight incubation in 50% ethanol followed by a 4 hour incubation in water. Samples were dried in a 60° C. oven for 16 hours before their weights were determined using a microbalance. Quadruplicate samples of each treatment were analysed in all experiments.

Free radical-mediated graft polymerization of AA, AM, HEMA, and PEGMA occurred on silicone surfaces when photo-initiator-coated samples were placed in aqueous solutions of monomer and exposed to UV light (FIG. 1). Grafting levels of nearly 1 mg/cm2 were achieved with as little as 2 minutes of irradiation time (FIG. 1A) using aqueous acrylic acid (5 wt %). The level of grafting could be controlled by adjustment of photo-initiator and monomer concentrations, as well as duration of irradiation (FIG. 1B). Table 1 shows grafting of acrylic acid monomer to silicone polymer surface. The grafting of acrylic acid monomer is shown in milligrams (AA) per cm2 of silicone polymer surface. In the presence of BPB grafting is 3.0 mg/cm2, 3.9 mg/cm2 and 2.3 mg/cm2 respectively, for silastic tubing, all silicone Foley catheters and a silicone rubber disk.

TABLE 1

Grafting extent of selected samples with respect to silicone source and photo-initiator identity.

| Sample | Photo-initiator (100 mM) | Monomer (694 mM) | g-Polymer (mg/cm$^2$) |
|---|---|---|---|
| Silastic Tubing | BPB | AA | 3.0 ± 0.1 |
| Foley Catheter | BPB | AA | 3.9 ± 0.2 |
| Disk | BPB | AA | 2.3 ± 0.1 |
| Disk | BBA | AA | 0.05 ± 0.04 |

Surface Characterization.

Figure 3:
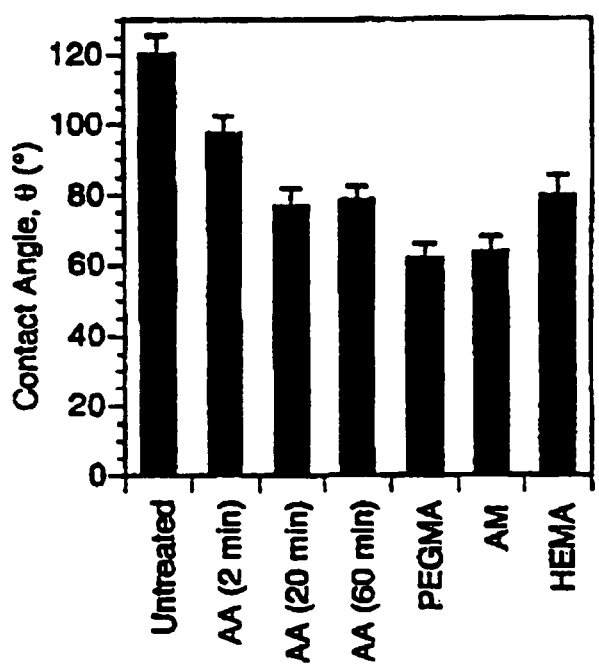
FIG. 3 shows the water contact angles of various types of surface modified silicone measured by the axisymmetric drop shape analysis technique. Samples were coated with 100 mM BPB and exposed to UVA light for 20 minutes unless otherwise noted.

Silicone disk samples were kept in an atmosphere of high relative humidity for 24 hours prior to room temperature water contact angle measurements using axisymmetric drop shape analysis. Images of sessile water drops were digitized and contact angles determined by minimizing the difference between the proscribed drop volume and the drop volume calculated from the contact diameter of the drop in conjunction with the Laplace equation of capillarity (17) (FIG. 3). A total of 8 measurements on four different surfaces were performed for each treatment.

Figure 4:
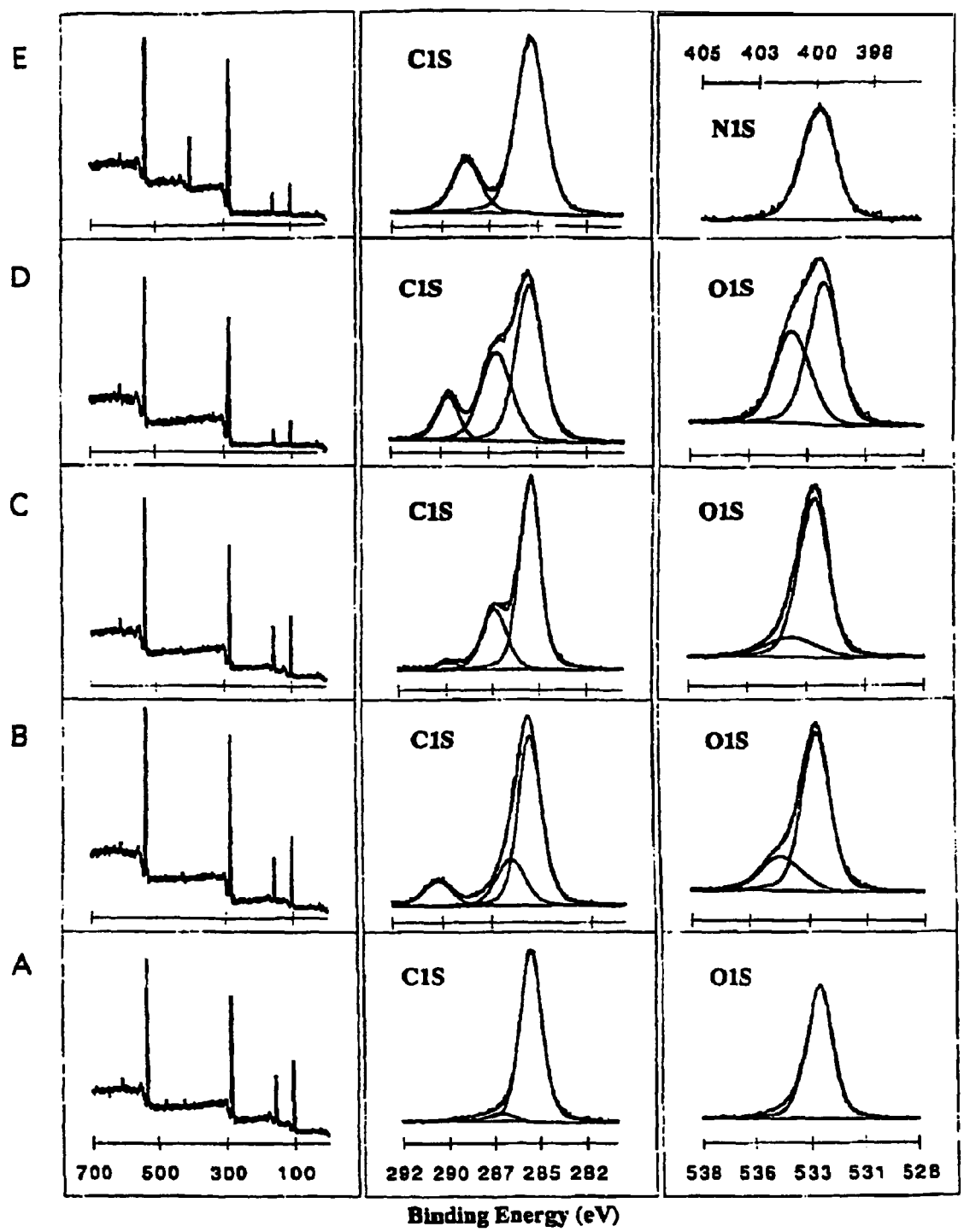
FIG. 4 shows low and high resolution XPS spectra of (A) PDMS, (B) PDMS-g-poly (AA), (C) PDMS-g-poly (polyethylenglycol methacrylate [PEGMA]), (D) PDMS-g-poly (hydroxyethyl methacrylate [HEMA]) and (E) PDMS-g-poly (acrylamide [AM]). Samples were obtained from 100 mM BPB pre-coating and 20 min UVA exposure time.

XPS spectra were recorded on a Leybold MAX 200 XPS system utilizing an unmonochromatized Mg K x-ray source operating at 12 kV and 25 mA with a take-off angle of 90°. Energy range was calibrated against Cu 2p3/2 and Cu 3p at 932.7 eV and 75.1 eV, respectively, and scaled to place the main C peak at 285.0 eV. Binding energy determination and deconvolution of spectra were accomplished using the curve-fitting routines provided with the spectrometer. XPS spectra from two separate samples were recorded for each type of surface modification (FIG. 4).

Example 2

Preparation of Modified Poly-AA Lubrious Silicone Surface and the Lubricious Poly-AA-Silver Salt Modified Silicone Surface Silicone foley catheters coated with a lubricious poly (AA) coating containing silver ion was prepared in accordance with the following steps:
1. The silicone sheet or catheter portion was incubated in methanolic solution of photo-initiator (BPB; 20-250 mM, preferably 75 mM) for 1 hour at room temperature in the dark.
2. The catheters were removed from the BPB solution and air dried at room temperature for 1 hour.
3. The silicone material was placed in aqueous solution containing acrylate monomer (0.1-1.5 M, preferably 0.7 M of acrylic acid) to which was added a small amount of BPB (10-50 µg/mL; preferably 20 µg/mL).
4. The solution was bubbled with nitrogen while exposing the silicone material to 350 nm light (from 2 to 60 minutes, preferably 10 minutes.)
5. The surface modified silicone was placed in 50% ethanol for one hour followed by immersion in borate buffer (pH 9.0) overnight.
6. The lubricious surface-modified silicone was briefly washed in distilled water and placed in sodium lactate solution (200-1000 mM, preferably 500 mM) for a short period (2-120 minutes, preferably 20 minutes).
7. The surface modified silicone was placed in aqueous silver lactate solution (1-50 mM, preferably 10 mM) for 20 minutes. The modified silicone surface contains the silver salt bound to the acrylate coating and dissolved in the water associated with the coating.

The silicone material may alternatively be placed in aqueous silver lactate solution (2-200 mM, preferably 150 mM) and autoclaved at 15 psi for 20 minutes to yield silver lactate bound to the acrylate coating which is non-lubricious but anti-microbial acrylate coating.

Figure 5:
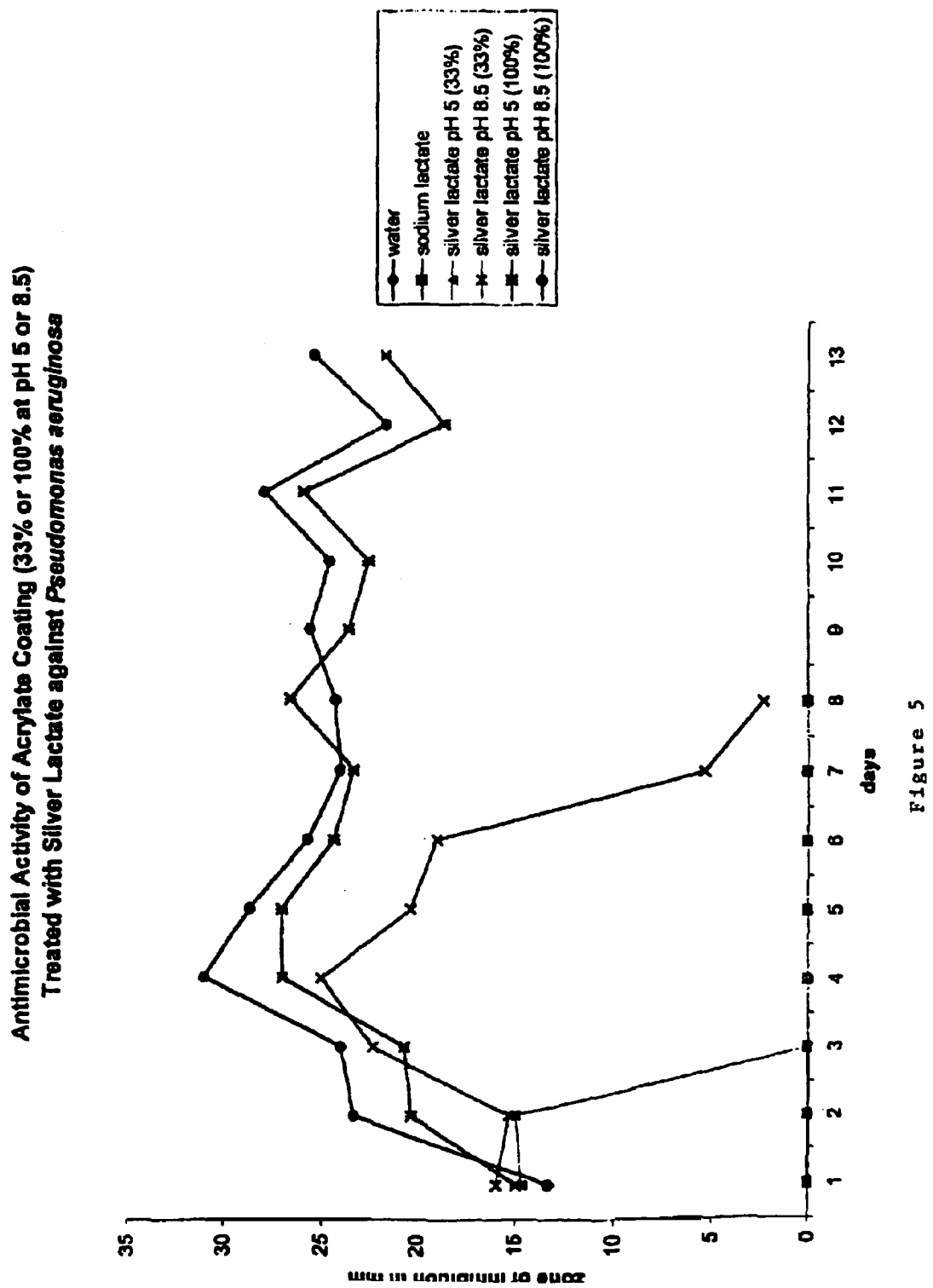
FIG. 5 illustrates the anti-microbial activity of the polyacrylate-silver coating on silicone against Pseudomonasaeruginose.

FIG. 5 illustrates the anti-microbial activity of the poly-acrylate-silver coating on silicone against Pseudomonasaeruginose. The greatest anti-microbial activities were produced by loading silver lactate in pH 5 and pH 8.5 solutions onto the surface of the silicone treated with 100% acrylate. Loading of silver salts at pH values higher or lower than those taught herein produce a surface showing substantial anti-microbial activity.

Figure 6:
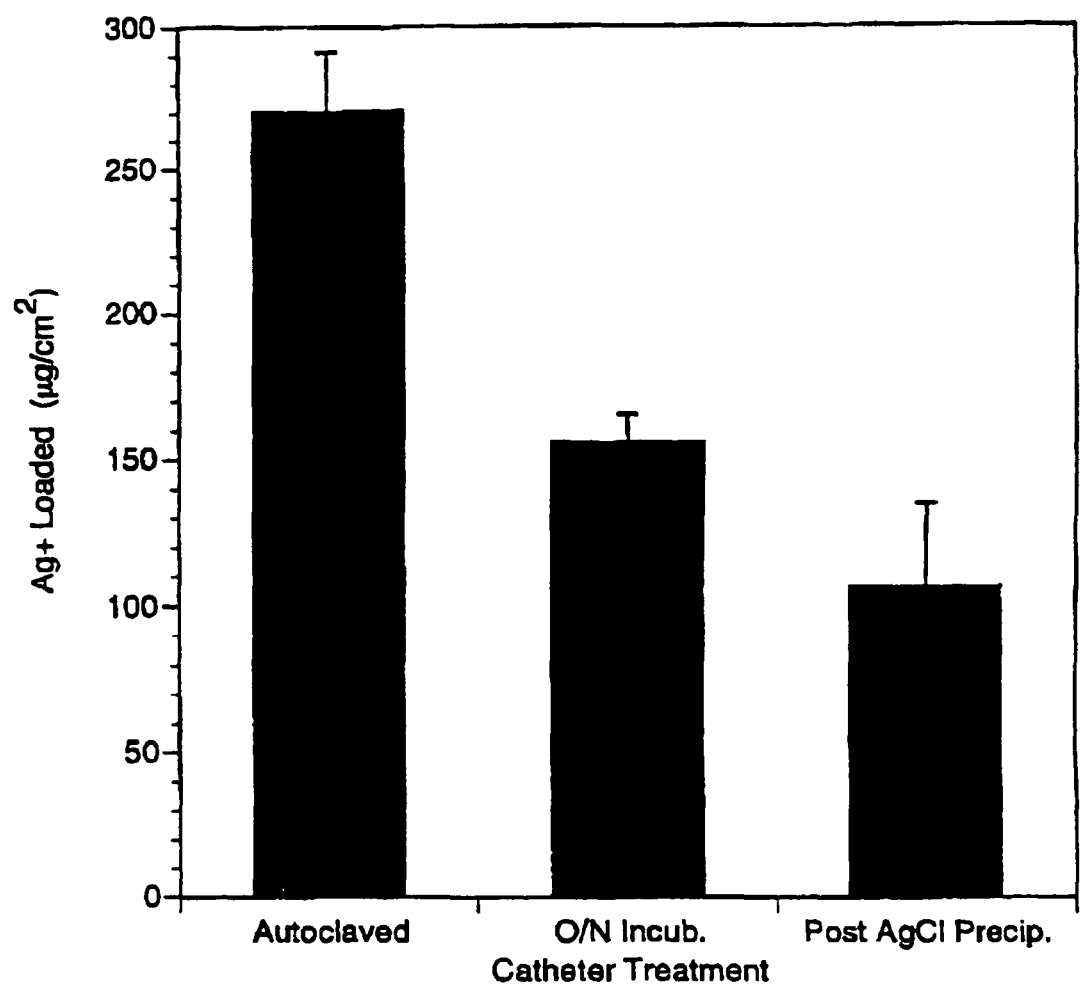
FIG. 6 illustrates the initial loading of silver salt on poly (AA)-modified catheters obtained by autoclaving in 150 mM silver lactate (Autoclaved) solution, or incubating overnight (O/N incub.) or incubation in 150 mM Nacl overnight, followed by a 2 hour incubation in 150 mM silver lactate solution (AgCl precip.).

FIG. 6 shows the loading of silver salt, silver lactate, on poly-acrylic acid modified catheters.

Example 3

Poly-AA Coated Silicone Sheets and Catheters With Attached Gelatin-Polyethylene Hydrogel Containing Silver Chloride The poly (AA) coated silicone sheets and catheters with attached gelatin-polyethylene oxide hydrogel containing silver chloride were prepared as follows:
1. The relevant silicone material portion was incubated in methanolic solution of photo-initiator (BPB; 20-250 mM, preferably 75 mM) for 1 hour at room temperature in the dark.
2. The silicone was removed from the BPB solution and air dried at room temperature for 1 hour.
3. The silicone was placed in aqueous solution containing acrylate monomer (0.1-1.5 M, preferably 0.7 M of acrylic acid) to which was added a small amount of BPB (10-50 µg/mL; preferably 20 µg/mL).
4. The solution was bubbled with nitrogen while exposing silicone to 350 mm light (from 2 to 60 minutes, preferably 10 minutes).
5. The surface-modified silicone was placed in 50% ethanol and left overnight at room temperature with shaking.
6. The silicone was washed in distilled water for 4 hours.
7. The silicone was placed in carbodiimide solution (2-20 mg/mL preferably 5 mg/mL) for 10 minutes.
8. The catheter was removed and placed on rotating apparatus with the long axis rotating and the silicone sheets were placed on a flat surface.
9. A small volume of carbodiimide solution (preferably 10 µL/cm of catheter) was spread on the silicone surface.
10. The silver salt containing liposome hydrogel was prepared according to the following:
Composition:

| | |
|---|---|
| DPPC (50 mg/ml) | 500 mg |
| Cholesterol | 263.4 mg |
| Vitamin E | 14.7 mg |
| Silver lactate (150 mM) | 10.0 ml |

The DPPC, cholesterol and vitamin E was dissolved in 10 ml chloroform and evaporated in a round bottle for at least 4 hours. Then 10 ml silver lactate (150 mM) was added to the above lipid film formulation and then heated to 45° C. until completely dispersed. This was then frozen in liquid nitrogen and thawed at 45° C. This was repeated 5 times. The mixture was extruded through a 100 nm filter and the filtrate collected. This was repeated 5 times. The silver lactate containing liposome mixture appears as a cream or yellowish cream suspension. The silver liposome suspension was then adjusted to pH 2 with HCl to convert the silver lactate not retained within liposomes to silver chloride to which was added 10% gelatin (w/v). The mixture was then heated to 45° C. until the gelatin was completely dissolved. Then 6-9% bis(nitrophenyl)polyethylene glycol 3400 (NP-PEG), preferably 9% was added and the mixture heated to 45° C. to dissolve the NP-PEG.
11. Silver chloride gel was added to the silicone surface (10-200 µL/cm of catheter, preferably 75 µL/cm), while rotating the catheter, or to a 10 cm×10 cm2 silicone area was added 2-5 mL of silver chloride gel, preferably 1 mL and spread gel evenly over the surface.

12. Upon setting of the gel, the coated silicone was incubated at 4° C. for 10 minutes.

13. The coated silicone was then placed in borate buffer (200 mM; pH 9.0) for 1 hour.

14. The catheter was washed in saline solution for 2 hours replacing washing solution after 1 hour.

Figure 7:
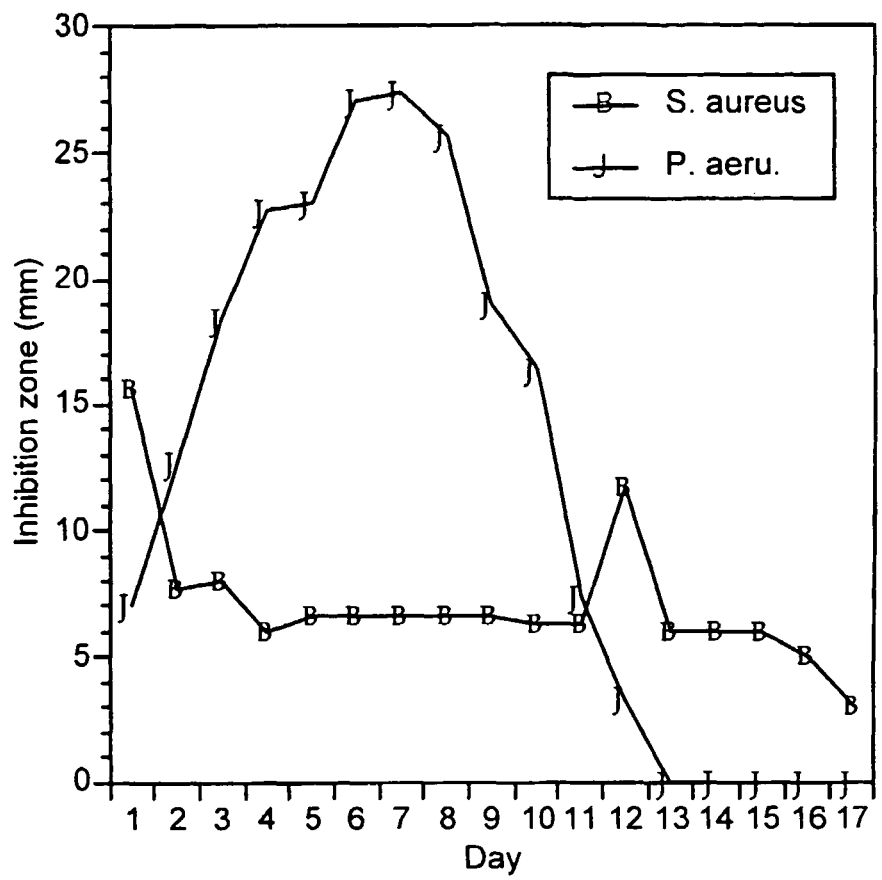
FIG. 7 illustrates the extended anti-microbial activity of gelatin-poly (ethylene oxide) coatings against Pseudomonasaeruginose and *Staphylococcus Aureus*.

FIG. 7 illustrates the anti-microbial activity of hydrogel coatings; liposome-150 mM silver lactate hydrogel (1: liposome silver hydrogel) as compared to hydrogel without silver lactate (2: control hydrogel), hydrogel dipped in solution of 150 mM silver lactate (3: silver hydrogel), and filter paper dipped in 150 mM silver lactate (4: silver filter paper), against Pseudomonasaeruginose and Methicillin resistant *Staphylococcus Aureus* (MRSA). Note that the width of test hydrogel was 20 mm. The same test sample was used and transferred daily to a new agar plate. The value reported for zone of inhibition is the "actual" diameter of the zone from which 20 has been subtracted.

Example 4

Preparation of Polyurethane Ureteral Stents coated With a Lubricious Poly (AA) Coating Containing Silver Ion Poly (AA)-silver coated stents were prepared as follows:

1. The polyurethane stent was incubated in methanolic solution of photo-initiator (DPA; 20-250 mM, preferably 100 mM) for 1 minute at room temperature in the dark.

2. The stents were removed from the DPA solution and air dried at room temperature for 30 minutes.

3. The stents was placed in a DPA-saturated aqueous solution containing acrylate monomer (0.1-1.5 M, preferably 0.7 M of acrylic acid).

4. The solution was bubbled with nitrogen while exposing the stents to 350 nm light (from 1 to 20 minutes, preferably 2 minutes.)

5. The surface modified silicone was washed in 50% ethanol for 1 hour followed by immersion in borate buffer (pH 9.0) overnight.

6. The lubricious surface-modified polyurethane material was then briefly washed in distilled water and placed in sodium lactate solution (200-1000 mM, preferably 500 mM) for a short period (2-120 minutes, preferably 20 minutes).

7. The surface-modified stent was immersed in aqueous silver lactate solution (1-50 mM, preferably 10 mM) for 1 minute.

The modified polyurethane surface contains silver ion bound to the acrylate coating and dissolved in the water associated with the coating. The lubricity of the coating relative to unmodified polyurethane is illustrated in Table 2. Also, note the relatively non-lubricious nature of non-ionized poly (AA) coatings and ionized poly (AA) coatings that were not dipped in sodium lactate before immersion in silver solution.

TABLE 2

Lubricity of polyurethane stents (7 French) with and without polyacrylate (PAA) coatings.

| Sample | Friction (N) |
| --- | --- |
| Unmodifed | 3.3 ± 0.2 |
| PAA (ionized) | 0.45 ± 0.08 |

TABLE 2-continued

Lubricity of polyurethane stents (7 French) with and without polyacrylate (PAA) coatings.

| Sample | Friction (N) |
| --- | --- |
| PAA (non-ionized) | 3.8 ± 0.5 |
| PAA + Ag-Lac. | (10 mM) 2.2 ± 0.5 |
| PAA + Na-Lac. + Ag-Lac. | (10 mM) 0.46 ± 0.11 |

Figure 8:
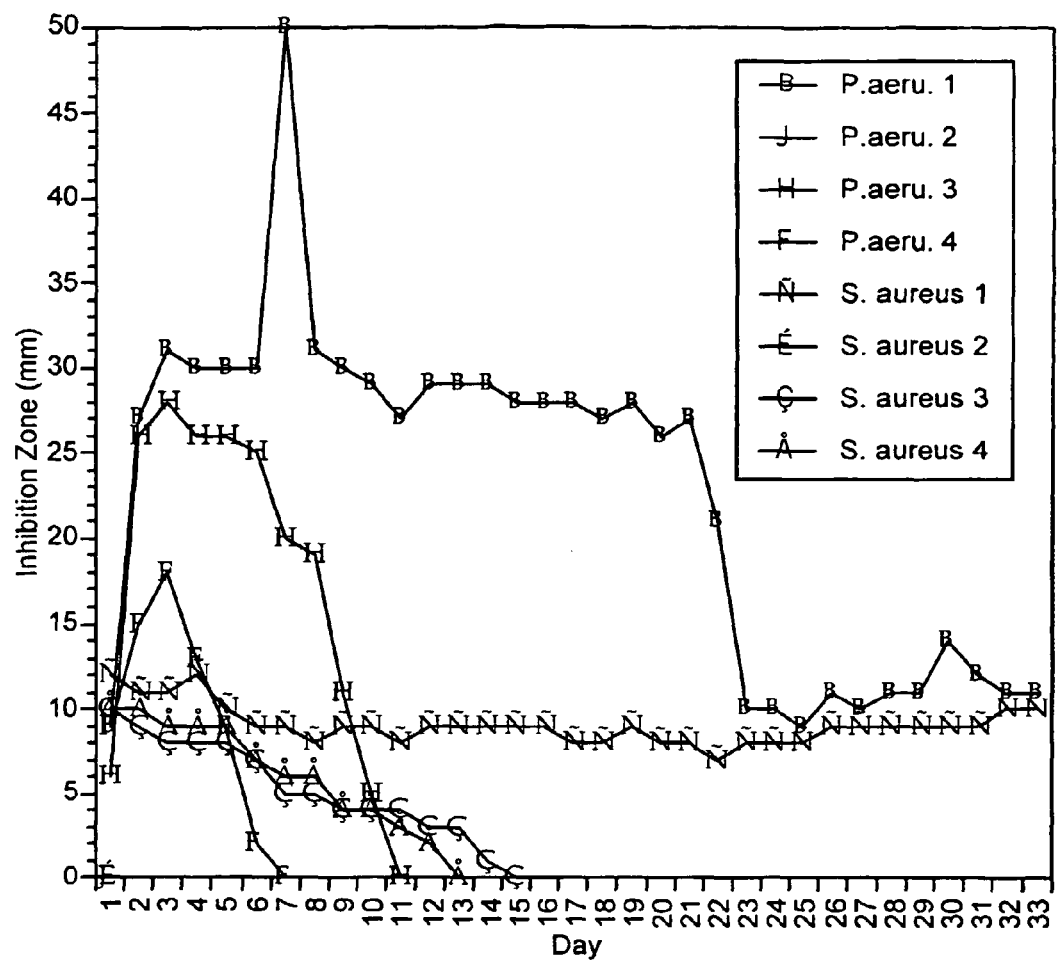
FIG. 8 illustrates the anti-microbial activity of the polyacrylate-silver coating on polyurethane stents against Pseudomonasaeruginose and *Staphylococcus Aureus*.

Anti-microbial activity of polyacrylate-silver coated stents is shown in FIG. 8. Growth inhibition zones were produced for extended periods with respect to both gram negative and positive species. Note that the width of stent pieces were approximately 2 mm. The same test sample was used and transferred daily to a new agar plate.

Although preferred embodiments of the invention have been described herein in detail, it will be understood by those skilled in the art that variations may be made thereto without departing from the spirit of the invention or the scope of the appended claims.

REFERENCES

1. Ikada, Y. and Uyama, Y., Surface Grafting. In *Lubricating Polymer Surfaces*. Technomic, Lancaster, Pa., 1993, pp. 111-137.
2. U.S. Pat. No. 4,585,666, Lambert, 1986.
3. U.S. Pat. No. 5,662,960, Hostettler, F., Rhum, D., Forman, M. R., Helmus, M. N., Ding, N., 1997.
4. U.S. Pat. No. 6,306,176, Whitbourne, R. J., 2001.
5. U.S. Pat. No. 5,160,790, Elton, R., 1992
6. U.S. Pat. No. 5,620,738, Fan, Y. L., Marlin, L., Bouldin, L. M., and Marino, L. M., 1997.
7. Saam, J. C.; Mettler, C. M.; Falender, J. R.; Dill, T. J., J. Appl. Polym. Sci. 1979, 24, 187.
8. Cameron, G. G.; Chisholm, M. S., Polymer 1985, 26, 437.
9. Holohan, A. T.; George, M. H.; Barrie, J. A., Makromol. Chem. Phys. 1994, 195, 2965.
10. Okada, T. and Ikada, Y., Makromol. Chem. 1991, 192, 1705.
11. Yang, J.-S. and Hsiue, G.-H., J. Appl. Polym. Sci. 1996, 61, 221.
12. Inoue, H. and Kohama, S., J. Appl. Polym. Sci. 1984, 29, 877.
13. Allmer, K.; Hult, A.; Ranby, B., J. Polym. Sci. A: Polym. Chem. 1988, 26, 2099.
14. Ulbricht, M.; Riedel, M.; Marx, U., J. Membr. Sci. 1996, 120, 239.
15. Saint, S; Elmore, J. G.; Sullivan, S. D.; Emerson, S. S.; Koepsell, T. D.; Am. J. Med. 1998, 105:236-241.
16. Zhang, J. Y.; Esrom, H.; Boyd, I. W., Appl. Surf Sci. 1999, 138-139, 315.
17. Moy, E.; Chenga, P.; Policova, Z.; Treppo, S.; Kwok, D.; Mack, D. R.; Sherman, P. M.; Neumann, A. W., Colloids Surfaces 1991, 58, 215.

The invention claimed is:

1. An anti-microbial polymeric composite comprising:
a polymeric body made of a polymeric material selected from the group consisting of polyurethanes, polyamides, polyesters, polyethers, polyorganosiloxanes, polysulfones, polytetrafluoroethylene and polysiloxanes, said polymeric body having a stable hydrophilic polyacrylate coating permanently grafted to the surface of the polymeric body, said coating being ionized and then cation saturated to render it lubricious, and said coating having a silver agent that is released from said polyacrylate coating slowly and continuously for a long and effective period of time.

2. The polymeric composite of claim 1, wherein said polymeric material is polysiloxane and said polysiloxane is silicone.

3. The polymeric composite of claim 2, wherein said polymeric material is provided as a device selected from the group consisting of implants, catheters, stents, wound dressings, cardiac valves, tubings, pins and clips.

4. The polymeric composite of claim 3, wherein said silver agent comprises a silver salt selected from the group consisting of silver lactate, silver phosphate, silver citrate, silver acetate, silver benzoate, silver chloride, silver carbonate, silver iodide, silver iodate, silver nitrate, silver laurate, silver sulfadiazine, silver palmitate and mixtures thereof.

5. The polymeric composite of claim 4, wherein said stable polyacrylate coating is made by the free radical polymerization of a monomer selected from the group consisting of acrylic acid, methacrylic acid, 2-carboxyethyl acrylate, 4-vinylbenzoic acid, itaconic acid, and mixtures thereof.

6. An anti-microbial polymeric composite comprising:
a polymeric body made of a polymeric material of silicone, said polymeric body having a stable hydrophilic polyacrylate coating permanently grafted to the surface of the polymeric body, said coating being ionized and then cation saturated to render it lubricious, and said coating having a silver agent that comprises a silver salt selected from the group consisting of silver lactate, silver phosphate, silver citrate, silver acetate, silver benzoate, silver chloride, silver carbonate, silver iodide, silver iodate, silver nitrate, silver laurate, silver sulfadiazine, silver palmitate and mixtures thereof.

7. An anti-microbial polymeric composite comprising:
a polymeric body made of a polymeric material selected from the group consisting of polyurethanes, polyamides, polyesters, polyethers, polyorganosiloxanes, polysulfones, polytetrafluoroethylene and polysiloxanes,
said polymeric body is provided as a device selected from the group consisting of implants, catheters, stents, wound dressings, cardiac valves, tubings, pins and clips,
said polymeric body having a stable hydrophilic polyacrylate coating permanently grafted to the surface of the polymeric body, said coating being ionized and then cation saturated to render it lubricious, and said coating having a silver agent that comprises a silver salt selected from the group consisting of silver lactate, silver phosphate, silver citrate, silver acetate, silver benzoate, silver chloride, silver carbonate, silver iodide, silver iodate, silver nitrate, silver laurate, silver sulfadiazine, silver palmitate and mixtures thereof.

8. The composite of claim 7, wherein said stable polyacrylate coating is made by the free radical polymerization of a monomer selected from the group consisting of acrylic acid, methacrylic acid, 2-carboxyethyl acrylate, 4-vinylbenzoic acid, itaconic acid, and mixtures thereof.

9. The composite of claim 6 or 7, wherein said lubricious coating is maintained when said composite is clinically used in vivo.

10. The composite of claim 1, wherein said coating is ionized using an aqueous base solution.

11. The composite of claim 10, wherein said cations are provided by a solution selected from the group consisting of sodium lactate, sodium citrate, disodium phosphate, potassium lactate, potassium citrate, dipotassium phosphate and mixtures thereof.

12. The composite of claim 1, wherein said lubricious coating is maintained when said composite is clinically used in vivo.

13. The composite of claim 2, wherein said silicone is silicone rubber.

14. The composite of claim 6, wherein said silicone is silicone rubber.

15. The composite of claim 7, wherein said wherein said polymeric material is polysiloxane and said polysiloxane is silicone rubber.

* * * * *